(12) United States Patent
Ramstein et al.

(10) Patent No.: US 8,652,046 B2
(45) Date of Patent: Feb. 18, 2014

(54) PALPATION ALGORITHMS FOR COMPUTER-AUGMENTED HAND TOOLS

(75) Inventors: Christophe Ramstein, San Francisco, CA (US); Christopher J. Ullrich, Santa Cruz, CA (US); Juan Manuel Cruz-Hernandez, Montreal (CA); Danny A. Grant, Laval (CA)

(73) Assignee: Immersion Corporation, San Jose, CA (US)

( * ) Notice: Subject to any disclaimer, the term of this patent is extended or adjusted under 35 U.S.C. 154(b) by 1165 days.

(21) Appl. No.: 12/354,186

(22) Filed: Jan. 15, 2009

(65) Prior Publication Data

US 2010/0179423 A1 Jul. 15, 2010

(51) Int. Cl.
*A61B 8/00* (2006.01)
(52) U.S. Cl.
USPC .................... 600/438; 600/407; 600/437
(58) Field of Classification Search
USPC .................... 600/407, 437–461, 587, 595
See application file for complete search history.

(56) References Cited

U.S. PATENT DOCUMENTS

| | | | |
|---|---|---|---|
| 5,389,849 A | 2/1995 | Asano et al. | |
| 5,609,607 A | 3/1997 | Hechtenberg et al. | |
| 5,833,634 A * | 11/1998 | Laird et al. | 600/587 |
| 5,836,894 A | 11/1998 | Sarvazyan | |
| 5,965,880 A | 10/1999 | Wolf et al. | |
| 5,989,199 A | 11/1999 | Cundari et al. | |
| 6,726,638 B2 * | 4/2004 | Ombrellaro | 600/587 |
| 2001/0031934 A1 | 10/2001 | Sarvazyan et al. | |
| 2002/0143275 A1 | 10/2002 | Sarvazyan et al. | |
| 2006/0152885 A1 | 7/2006 | Hewit et al. | |

OTHER PUBLICATIONS

International Search Report for corresponding PCT Application No. PCT/US2010/020011 mailed Apr. 7, 2010.

* cited by examiner

*Primary Examiner* — Tse Chen
*Assistant Examiner* — Mark Remaly
(74) *Attorney, Agent, or Firm* — Miles & Stockbridge P.C.

(57) ABSTRACT

A method and system for performing minimally invasive tissue examination with a computer-assisted hand tool. The computer-assisted hand tool is moved into contact with the tissue under examination. An indication is received from a first sensor in the computer-assisted hand tool of each feature detected in a time interval during movement of the hand tool in contact with the tissue under examination. Each feature detected in the preset time interval is processed to determine a haptic feedback to provide to the user. A haptic feedback is generated and provided to the user via an actuator that is responsive to at least one feature detected in the time interval.

21 Claims, 8 Drawing Sheets

PALPATION ALGORITHMS FOR COMPUTER-AUGMENTED HAND TOOLS

CROSS-REFERENCE TO RELATED APPLICATION

The present patent application is related to U.S. application Ser. No. 11/955,563, entitled "Minimally Invasive Surgical Tools with Haptic Feedback," filed on Dec. 13, 2007, and having the same assignee. This application is incorporated by reference herein.

TECHNICAL FIELD

Embodiments of the invention relate generally to computer-augmented hand tools and, more specifically, to computer-augmented hand tools for performing tissue examination of patients during minimally invasive procedures and providing haptic feedback.

BACKGROUND INFORMATION

In existing surgical practice, surgeons must use their finger tips to identify obscured vasculature. In a minimally invasive context, this is accomplished through the use of a hand port. A hand port is a sealable insert that permits surgeons to insert their entire hand into the peritoneum and manipulate tissues, palpate, etc. A critical disadvantage of this approach is that it leaves the patient with a 6-8 cm incision scar with attendant post-operative pain and increased infection/complications.

In minimally invasive surgical (MIS) procedures, surgeons use long thin instruments to manipulate tissues through small "keyhole" incisions in the patient. MIS procedures typically have dramatically reduced recovery times as compared to non-minimal counterparts. A key disadvantage of MIS tools is that they are challenging for the surgeons to use correctly and they significantly minimize the capability to directly experience the anatomy at the distal tip of the instrument. Some have addressed this problem by displaying information gathered at the distal end of the surgical tool visually, or by using complex shape deformation displays.

SUMMARY

In one embodiment of the invention, a method is provided for performing minimally invasive tissue examination with a computer-assisted hand tool. The computer-assisted hand tool is moved into contact with the tissue under examination. An indication is received from a first sensor in the computer-assisted hand tool of each feature detected in a time interval during movement of the hand tool in contact with the tissue under examination. Each feature detected in the time interval is processed to determine a haptic feedback (e.g., tactile effect) to provide to the user. A haptic feedback is generated and provided to the user via an actuator that is responsive at least to the number of peaks detected in the preset time interval.

In some embodiments, an indication is received from a second sensor in the computer-assisted hand tool of an acceleration of the computer-assisted hand tool in contact with the tissue under examination. The acceleration of the computer-assisted hand tool is compared with a threshold acceleration. The number of peaks in a portion of a power spectrum is determined when the acceleration of the hand tool is less than the threshold acceleration.

BRIEF DESCRIPTION OF THE DRAWINGS

These and other advantages and aspects of the exemplary embodiments will become apparent and more readily appreciated from the following detailed description of the embodiments taken in conjunction with the accompanying drawings, as follows.

DETAILED DESCRIPTION

The following description is provided as an enabling teaching of exemplary embodiments. Those skilled in the relevant art will recognize that many changes can be made to the embodiments described, while still obtaining the beneficial results. It will also be apparent that some of the desired benefits of the embodiments described can be obtained by selecting some of the features of the embodiments without utilizing other features. Accordingly, those who work in the art will recognize that many modifications and adaptations to the embodiments described are possible and may even be desirable in certain circumstances, and are a part of the invention. Thus, the following description is provided as illustrative of the principles of the embodiments and not in limitation thereof, since the scope of the invention is defined by the claims.

The embodiments disclosed include palpation algorithms for computer augmented hand tools (CAHT) or robotic surgical devices. The palpation algorithms are based on the manner in which surgeons would palpate tissue in open surgery, allowing intuitive use of the surgical hand tools. Regular hand tools include laparoscopic graspers, scissors, endovascular catheters, endoscopes, and single port devices. A CAHT includes a regular hand tool enhanced with electronic functionalities, such as additional sensors, processing resources, graphical displays, haptic feedback, and audio feedback. Sensors can include, but are not limited to, accelerometers, contact sensors, pressure sensors, and proximity sensors. A CAHT enables surgeons to confirm easily a pulse candidate or tumors under the tool tip, even under some level of fat, and provide feedback in the form of a tactile or haptic pulse. In other embodiments, acoustic and graphical feedback can also be provided.

Figure 1A:
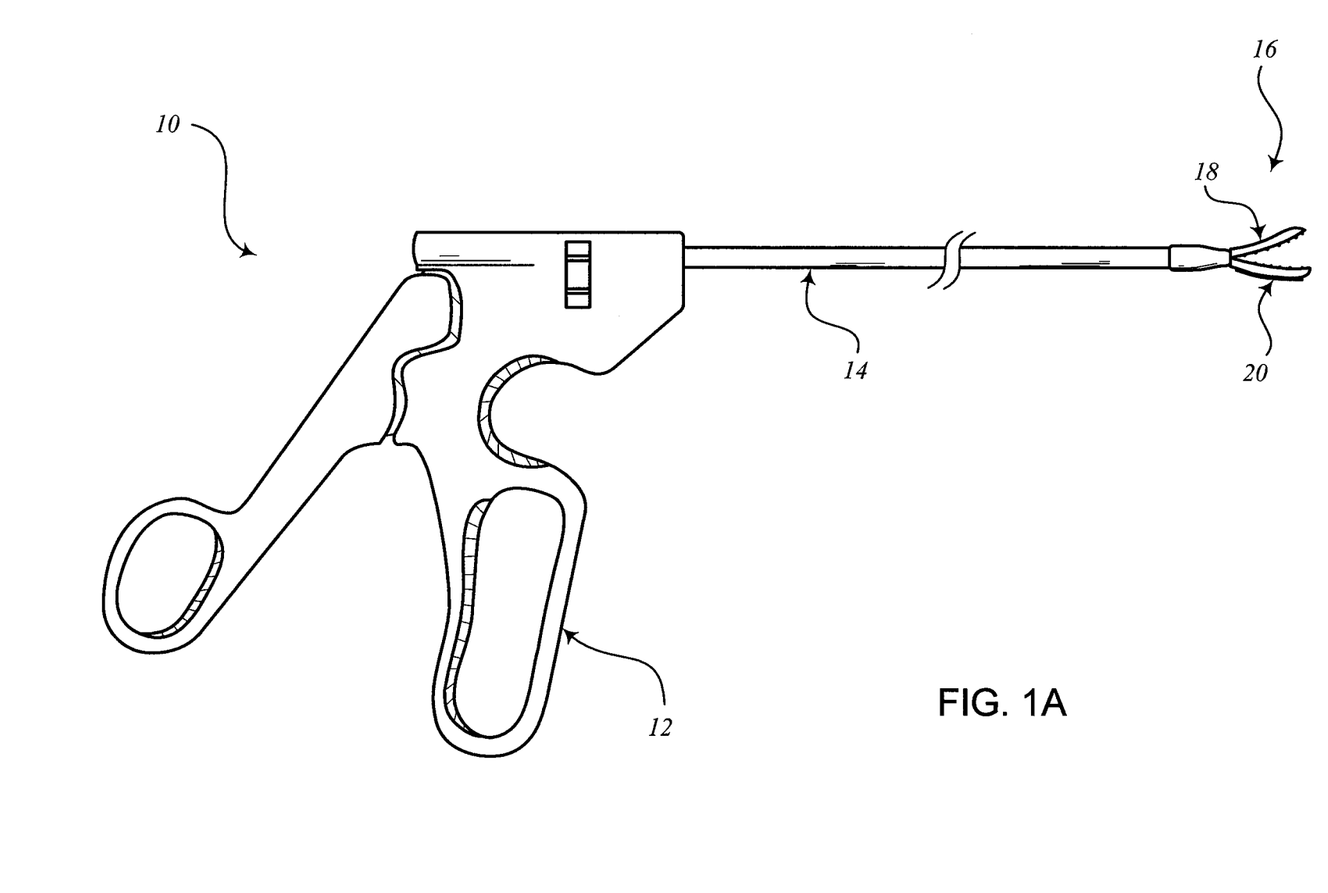
FIG. 1A illustrates a surgical hand tool having a sensor array in an exemplary embodiment.

FIG. 1A illustrates an exemplary embodiment of a CAHT 10. In this embodiment, CAHT 10 is depicted as a laparoscopic grasper that is configured to be inserted through a small incision in the abdomen of a patient. CAHT 10 includes a handle 12, a shaft 14, and an end portion 16. Shaft 14 connects handle 12 to end portion 16 and communicates mechanical actions of handle 12 to end portion 16. Shaft 14 communicates electrical signals received from end portion 16 to handle 12. As further depicted in FIG. 1, end portion 16 includes a tip 18 and a sensor array 20 formed on tip 18. End portion 16 can include any suitable type of tip having any suitable functionality. In some implementations, shaft 14 can be about 20 cm to 30 cm in length, and tip 18 can be about 10 mm to 15 mm in length. By manipulating handle 12, a user can insert end portion 16 into the abdomen of the patient. When end portion 16 is inserted, the user can further manipulate handle 12 to control the location and orientation of tip 18 such that sensor array 20 is able to contact certain regions of the patient. In some embodiments, the sensor array 20 can be configured as stiffness sensors that can detect nodules, such as tumors or other stiff regions. By processing the number of sensors contacting the stiff region, the relative stiffness that is sensed can be used to determine the size of a nodule and provide a haptic effect to the user to communicate the size of the nodule.

In other embodiments, the sensor array 20 can detect the location of blood vessels. Sensors in contact with a blood vessel detect the pulsing vessel. Adjacent sensors that are not in contact with the blood vessel experience a loss of contact with tissue due to the lifting action of the pulsing blood vessel on the sensors that are in contact with the blood vessel. In still other embodiments, the sensor array 20 can include piezoelectric sensors that generate ultrasound signals that reflect off luminal structures, such as, but not limited to, blood vessels, the gastrointestinal tract, and the respiratory tract. Echo signals can be detected by sensors 20 to determine the location of luminal structures. The ultrasound emission and echo measurement technique also can be useful for tumor tissue identification.

Figure 1B:
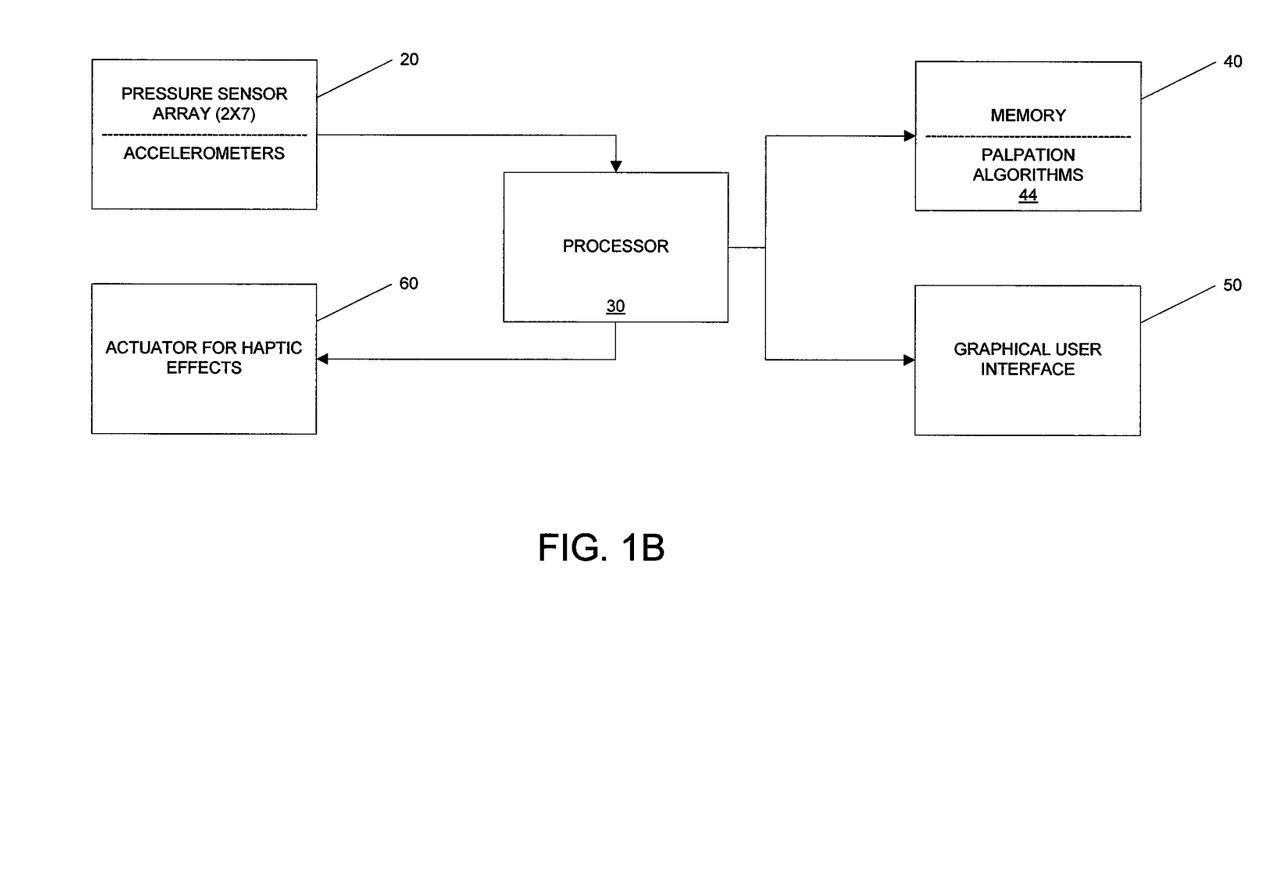
FIG. 1B illustrates a computer-assisted haptic system in which the palpation algorithms can be deployed in an exemplary embodiment.

FIG. 1B illustrates a system block diagram for a computer-assisted hand tool 10 in which the palpation algorithms can be deployed in an exemplary embodiment. The computer-assisted hand tool 10 includes a plurality of sensors 20 that can include accelerometers for detecting and measuring the acceleration of the tool, and a pressure sensor array for detecting pulses during movement of the tip of the tool on the tissue being palpated. Processor 30 receives signals from the sensors 20, and processes the received signals based on instructions stored in memory device 40. The instructions stored in memory device 40 include the palpation algorithms 44. Based on a "state" of the CAHT 10 determined during execution of the palpation algorithm 44 instructions, the processor 30 can have the actuator 60 in the CAHT play a haptic effect described herein as transient, periodic, and strong. It should be noted that the terms haptic effect also can be referred to as tactile effect, tactile feedback, haptic feedback, force feedback, vibrotactile feedback, haptic cues, thermal feedback, kinesthetic feedback, etc.; these terms including the representation of other physical properties (e.g., stiffness, viscosity).

The haptic effect played is characterized by one or more of the magnitude, frequency, and duration of the effect. The haptic effect can be dynamic based on a changing level of stiffness or deformation of the tissue being examined.

In an exemplary embodiment, the processor 30 can be a laptop or personal computer that is electrically coupled to the CAHT. The laptop or personal computer can have a graphical user interface (GUI) 50 that enables the user to select optional processing steps for the palpation algorithms. The GUI 50 could be similar to that illustrated in FIG. 9. Memory device 40 can be any type of storage device or computer readable medium capable of storing the instructions for the palpation algorithms. Memory 40 can include random access memory, read-only memory, etc.

In other embodiments, the processor 30 can be an application specific integrated circuit (ASIC) that is a component of the CAHT. In such embodiments, the instructions for the palpation algorithms 44 can be embedded in the processor 30.

In an exemplary embodiment, the sensor array can include a 2×7 array of pressure transducers. Each pressure transducer can be in contact with the tissue being palpated, therefore, each transducer is processed for pulses received. Each transducer can detect zero or more pulses in a time window. The actuator 60 can generate a vibration on the handle 12 of the CAHT 10. More specifically, the actuator 60 can include a force applying mechanism that applies a vibrotactile force to the CAHT user based on a level of stiffness or deformation of the tissue being examined. One parameter of the actuator that can be used in exemplary embodiments is the peak voltage applied during the playing of haptic effects.

Figure 2:
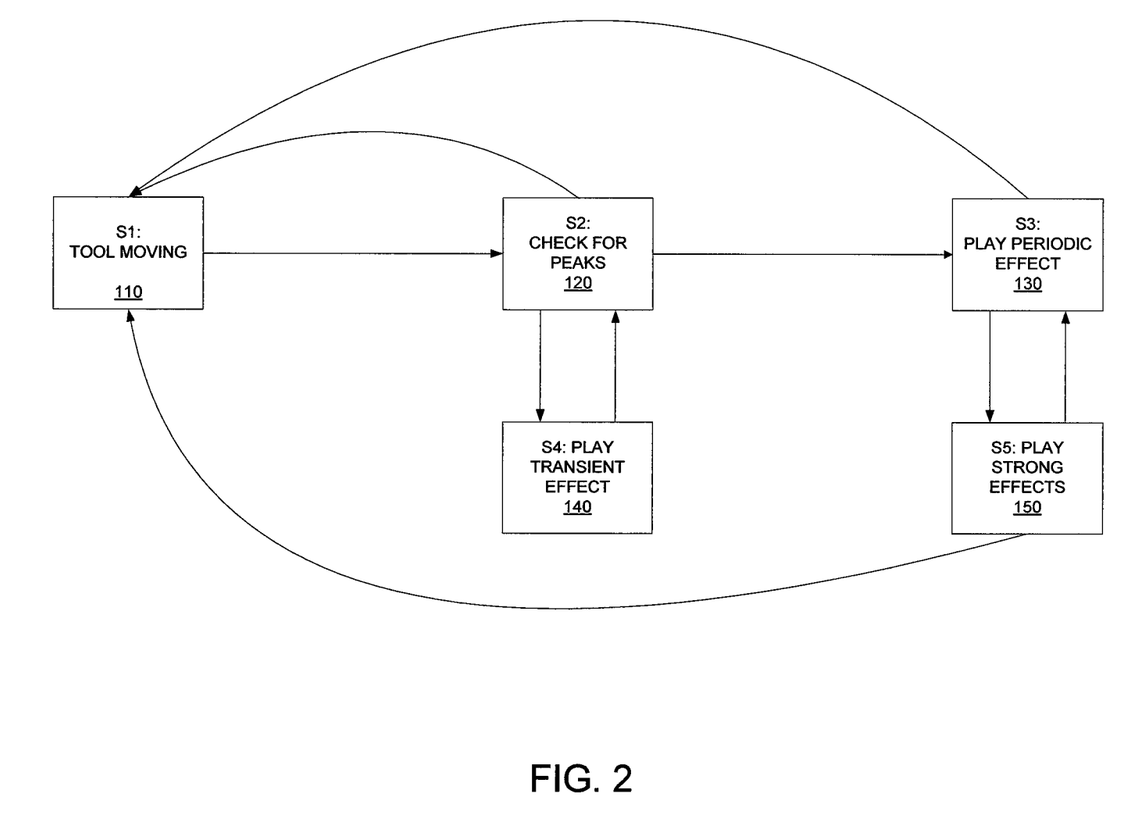
FIG. 2 illustrates a state machine transition diagram for the palpation algorithms in exemplary embodiments.

FIG. 2 illustrates a state machine transition diagram for the palpation algorithms in exemplary embodiments. The different states in the state machine are as follows: (a) state S1—tool moving; (b) state S2—check for peaks; (c) state S3—play periodic effect; (d) state S4—play transient effects; and (e) state S5—play strong effects. The state transitions and conditions for transition to different states are provided in Table 1.

TABLE 1

State Transitions

| Transition | Condition |
| --- | --- |
| S1 to S2 | Acceleration < Threshold |
| S2 to S1 | Acceleration > Threshold |
| S2 to S3 | More than one peak found with correct frequency |
| S2 to S4 | Signal peak found but period not yet identified |
| S3 to S1 | Acceleration > Threshold |
| S3 to S5 | Peaks of signals are within target power range |
| S4 to S2 | Effect played |
| S5 to S1 | Acceleration > Threshold |
| S5 to S3 | Peaks of signals are not in target power range |

The transient, periodic, and strong haptic effects that are described in exemplary embodiments can be implemented as follows:

haptic effect played=$M \times \sin(2 \times \pi \times (1/0.04) \times t)$ for $0 \leq t \leq 0.02$ sec where M is the peak voltage value supplied by the actuator. For a transient haptic effect, the value of M could be 3-5 in exemplary embodiments. The transient effect could be played at non-periodic time intervals, such as at times t0, t0+0.9 sec, t0+0.9+1.1 sec, etc. A periodic haptic effect could have the same value of M as for the transient effect, but the effect would be played at periodic time intervals, such as at times t0, t0+T, t0+2T, t0+3T, where T is the period. A strong periodic haptic effect would have a larger value of M (e.g., 6-9) than for either a transient or periodic effect. The strong haptic effect would be played at periodic intervals.

Figure 3:
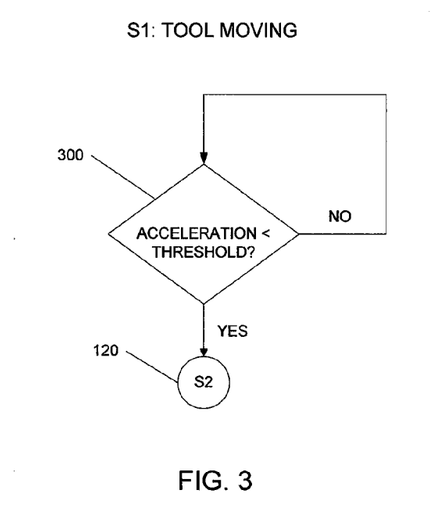
FIG. 3 illustrates the processing logic for state S1 (tool moving) in an exemplary embodiment.

FIG. 3 illustrates the processing logic for state S1 110 (tool moving). The state transitions from state S1 to state S2 120 (check for peaks), or remains in state S1 based on the acceleration of the CAHT 10 as measured by accelerometers in sensor 20. The acceleration of the moving CAHT 10 is compared to a threshold in decision block 300. For example, the threshold for a one dimensional acceleration signal could be 0.1 g peak to peak, where "g" is the standard measure of gravitational force. For a vector acceleration signal, this threshold could be the angle variation of the vector at a time t0 and the vector at a time t1, e.g., 0.1 radians/sec. If acceleration is less than the threshold, the state transitions to state S2 120 to check for peaks. If acceleration of the CAHT 10 equals or exceeds the threshold, the CAHT 10 remains in state S1 110.

Figure 4:
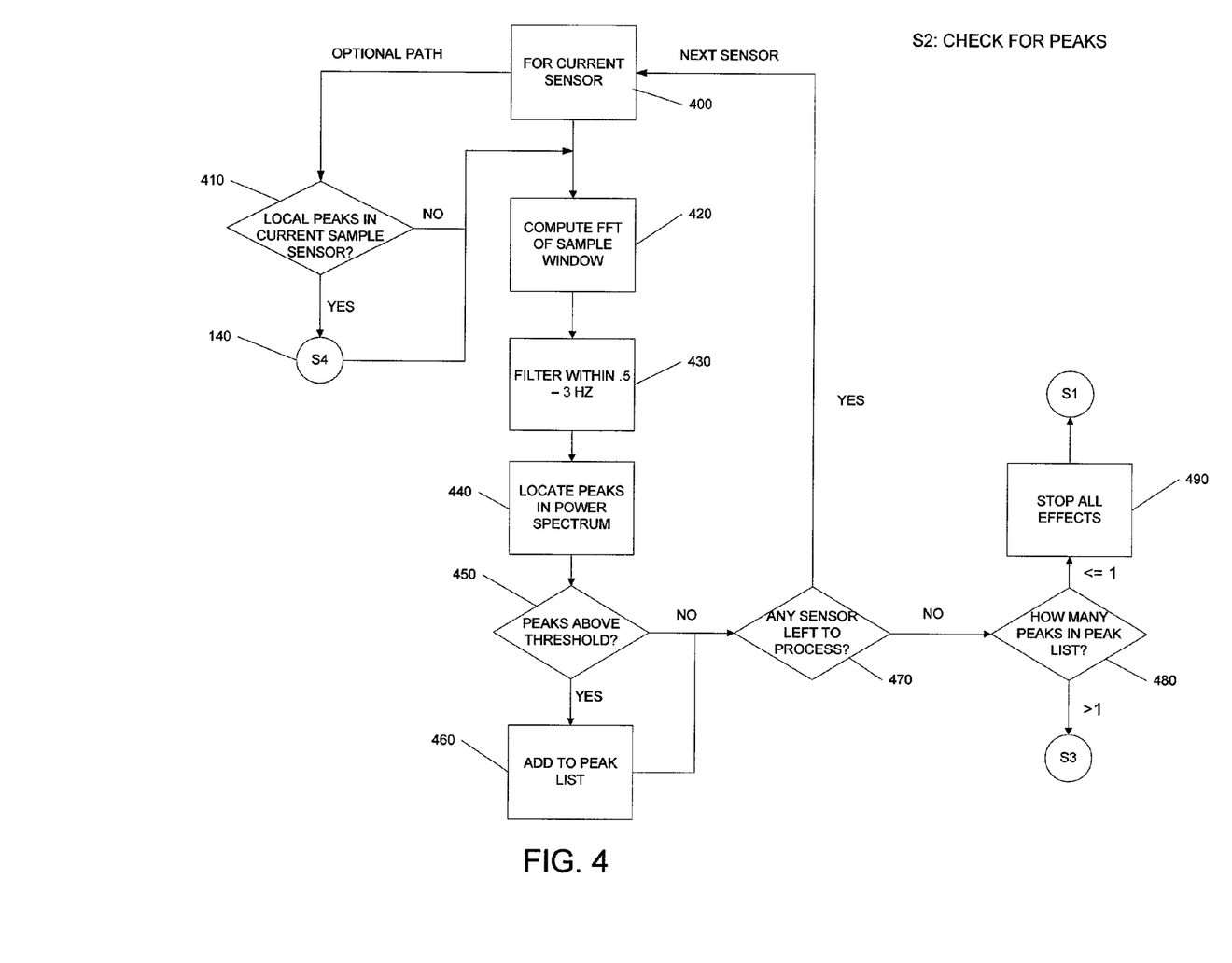
FIG. 4 illustrates the processing logic for state S2 (check for peaks) in an exemplary embodiment.

FIG. 4 illustrates the processing logic for state S2 120 (check for peaks). Processing begins for a sensor in the sensor array 20 as indicated in logic block 400. Each sensor in the sensor array 20 is processed. The main processing logic will be discussed first, and will be followed by discussion of the optional path from logic block 400. As indicated in logic block 420, a Fast Fourier Transform (FFT) is computed for the sensor signals detected during the sample window. In an exemplary embodiment, the window for the sample could be three seconds. The window duration should be long enough to receive several pulses to determine the frequency of the pulses. The result could then be filtered within the 0.5-3 Hz range. The peak signals in the power spectrum are then located as indicated in logic block 440.

In decision block 450, a determination is made as to whether or not the peaks are above a threshold amplitude or other parameter value associated with the peaks. If there are peaks that are above the threshold, they are added to the peak list in logic block 460. Processing then continues in decision block 470. If no peaks are above the threshold value in decision block 450, a determination is made in decision block 470 as to whether or not there are any sensors still left to process. If there are sensors remaining to be processed, processing then returns to logic block 400 for processing of the next sensor. If there are no sensors remaining to be processed, processing then continues in decision block 480 with the determination of the number of peaks above the threshold value in the peak list. If the number of peaks above threshold value exceeds one, the state transitions from state S2 120 to state S3 130 (play periodic effect). If the number of peaks above the threshold value is one or none, all effects are stopped as indicated in logic block 490. The state then transitions from state S3 back to S1 (tool moving).

Figure 9:
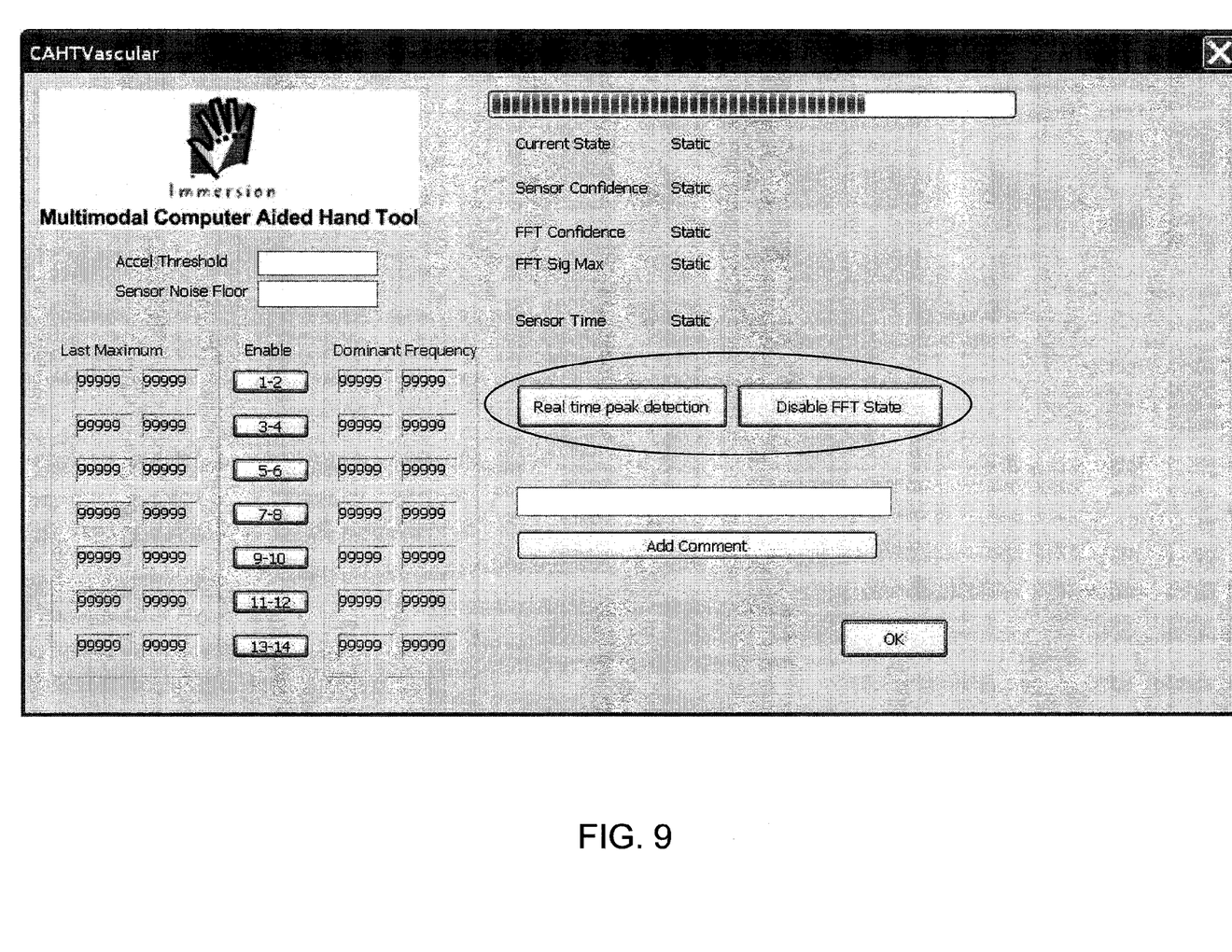
FIG. 9 illustrates a graphical user interface for presetting operation of the palpation algorithms in an exemplary embodiment.

There is an optional path in conjunction with state S2 shown in FIG. 4. For a current sensor in the sensor array, an optional path for the CAHT signal processing is to determine the local peaks, if any, in the current sample for the sensor, as indicated in decision block 410. This optional path can be selected by the user via a graphical user interface such as illustrated in FIG. 9 (selecting "real time peak detection"). If there are local peaks, then the state transitions from state S2 120 to state S4 140 (play transient haptic effects). If there are no local peaks, processing continues in logic block 420.

Figure 5:
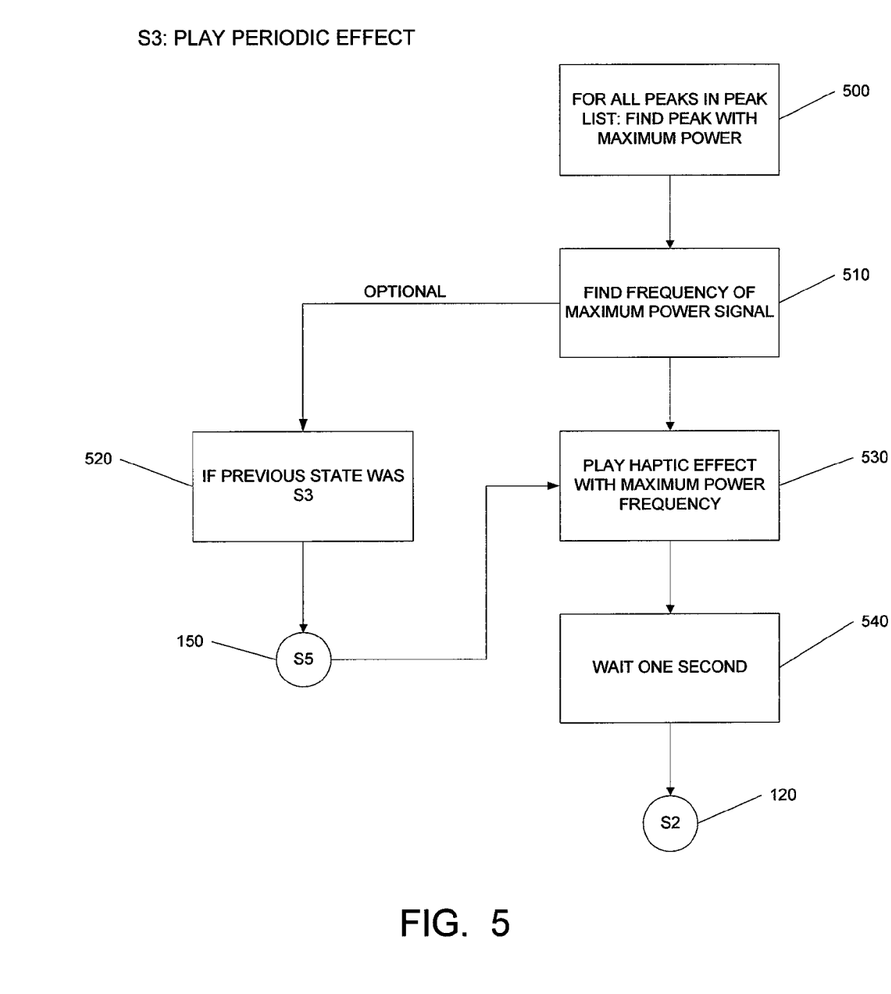
FIG. 5 illustrates the processing logic for state S3 (play periodic effect) in an exemplary embodiment.

FIG. 5 illustrates the processing logic for state S3 130 (play periodic effect). Processing for this state begins in logic block 500 by finding the peak in the peak list having the maximum power. The frequency of the maximum power signal is determined in logic block 510. A haptic effect at the frequency of the maximum power signal is then played as indicated in logic block 530. After a one second delay represented by logic block 540, the state transitions from state S3 130 to state S2 120 to continue checking the raw data that has been captured in parallel.

There is also an optional path in conjunction with state S3 shown in FIG. 5. After determining the frequency of the maximum power signal in logic block 510, an optional step is to determine if the previous state was S3 (play periodic effect) as indicated in logic block 520. If the previous state was S3, then the state transitions from state S3 130 to state S5 150 (play strong effects).

Figure 6:
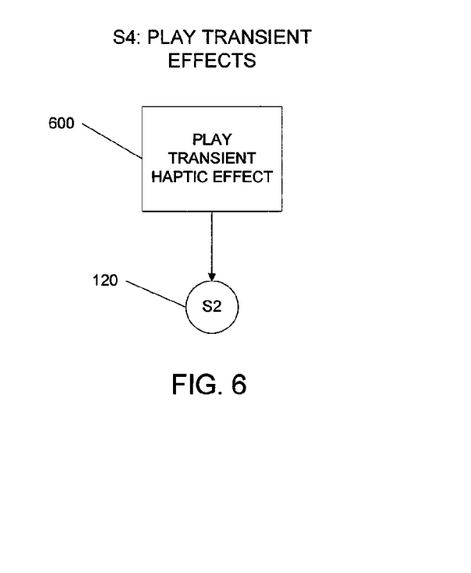
FIG. 6 illustrates the processing logic for state S4 (play transient effects) in an exemplary embodiment.

FIG. 6 illustrates the processing logic for state S4 (play transient effects). This figure simply shows that after the transient haptic effect is played as indicated by logic block 600, the state transitions from state S4 140 to state S2 120 (check for peaks).

Figure 7:
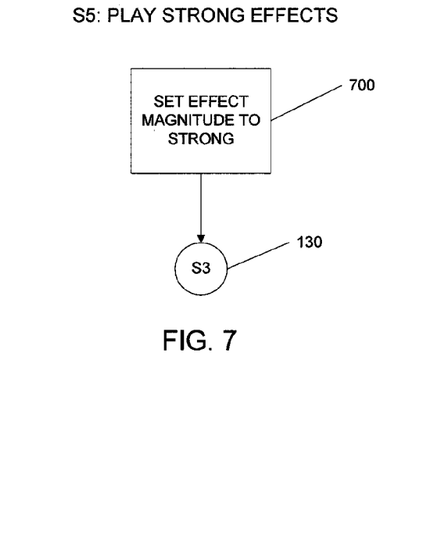
FIG. 7 illustrates the processing logic for state S5 (play strong effects) in an exemplary embodiment.

FIG. 7 illustrates the processing logic for state S5 150 (play strong effects). This figure simply shows that after the strong haptic effect is played as indicated by logic block 700, the state transitions from state S5 150 to state S3 130 (play periodic effect).

In the preceding discussion of state diagram processing logic, the term peak was used to explain an exemplary embodiment. More generally, the term "feature" can be used to encompass a plurality of embodiments. For example, in a tissue, the CAHT user could be looking not only for a pulse but also for the stiffness in a tissue. Therefore, the pulses and stiffness are considered features that are sensed by the CAHT 10.

Figure 8:
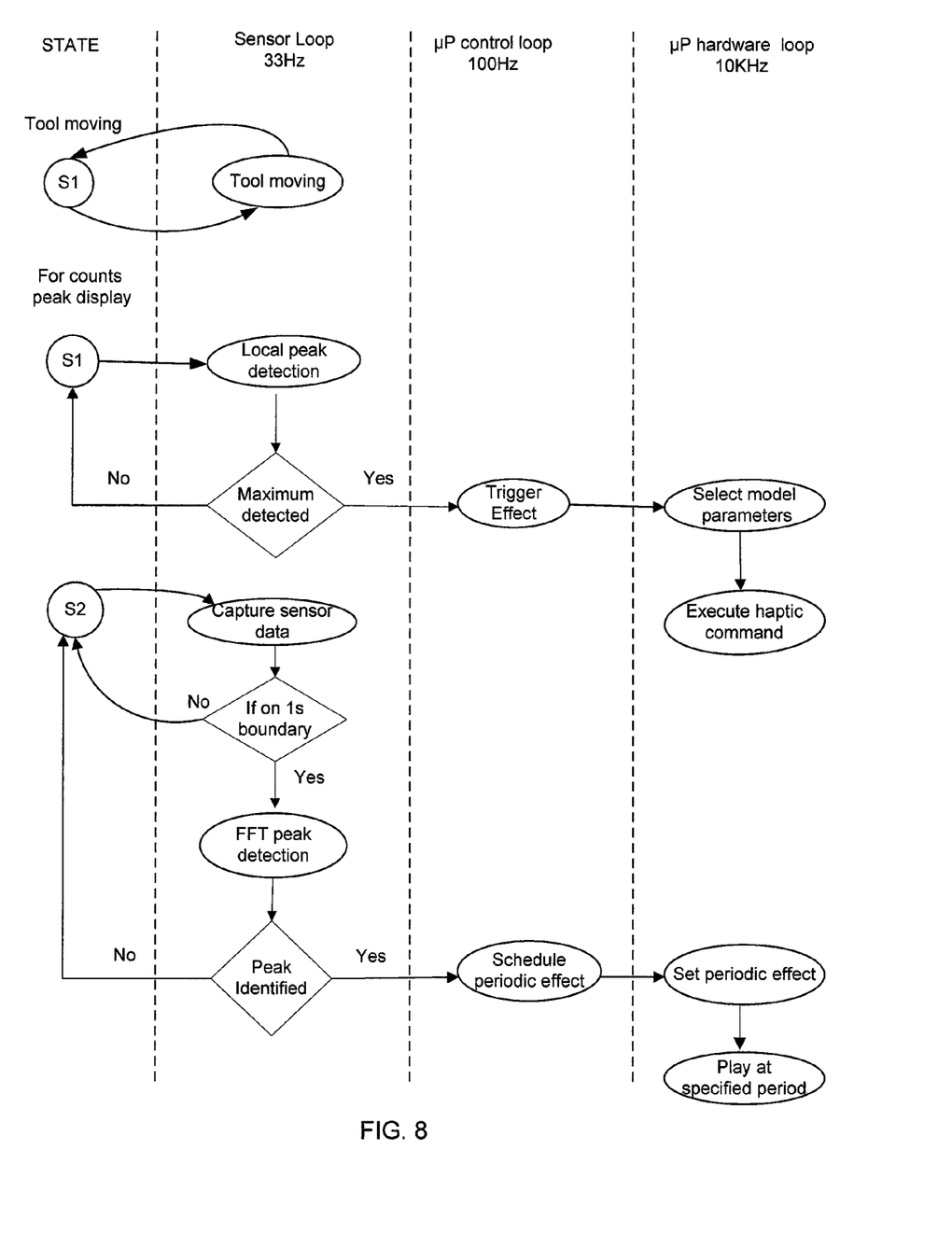
FIG. 8 illustrates the timer loops running in parallel in an exemplary embodiment.

FIG. 8 illustrates the timer loops running in parallel in an exemplary embodiment. There are three timer loops illustrated in the figure. The first timer loop is a sensor loop that could operate at 33 Hz in one embodiment. In the sensor loop, if in state 1, tool movement is detected (state 1), local peaks are detected (if optional step is enabled), and the maximum peak may be determined. In state 2, sensor data is captured, the FFT peak is detected and may be identified. The second timer loop is a microprocessor control loop that could operate at 100 Hz in one embodiment. In the microprocessor control loop, if the maximum peak is detected during local peak detection, a haptic effect is triggered. If the peak is identified during FFT peak detection (state 2), a periodic haptic effect is scheduled. The third timer loop is a microprocessor hardware loop that could operate at 10 KHz in one embodiment. This timer loop controls operation of the actuator. If a haptic effect is triggered in the microprocessor control loop, model parameters are selected in the microprocessor hardware loop, and haptic commands are executed by the actuator. If a periodic effect is scheduled in the microprocessor control loop, period effects are set and played by the actuator at a specified period in the hardware loop. The frequencies of operation for the three timer loops are provided by way of example, and are not a limitation of the embodiments disclosed.

FIG. 9 illustrates a graphical user interface for setting operation of the palpation algorithms in an exemplary embodiment. The "real time peak detection" button enables the detection of local peaks in real time. The "disable FFT state" button disables the complex path to peak detection illustrated in FIG. 4. The playing of a stronger haptic effect can be implemented in software only, or can be exposed on a separate or a modified graphical user interface such that the effect can be enabled or disabled.

The system and method embodiments have been described as computer processes that are implemented in hardware, software, or a combination of hardware and software. It is important to note, however, that those skilled in the art will appreciate that the palpation algorithms of the disclosed embodiments are capable of being distributed as a computer readable medium in a variety of forms, regardless of the particular type of physical signal bearing media utilized to carry out the distribution. Examples of physical signal bearing media include, without limitation, recordable-type media such as flash drives, portable hard drives, diskettes, and CD ROMs.

The corresponding structures, materials, acts, and equivalents of all means plus function elements in any claims below are intended to include any structure, material, or acts for performing the function in combination with other claim elements as specifically claimed.

Those skilled in the art will appreciate that many modifications to the exemplary embodiments are possible without departing from the scope of the invention. In addition, it is possible to use some of the features of the embodiments described without the corresponding use of the other features. Accordingly, the foregoing description of the exemplary embodiments is provided for the purpose of illustrating the principles of the invention, and not in limitation thereof, since the scope of the invention is defined solely by the appended claims.

What is claimed is:

1. A method for performing tissue examination with a computer-assisted minimally invasive hand tool, comprising the steps of:
moving the computer-assisted hand tool into contact with a tissue under examination;
receiving and processing a plurality of signals from one or more sensors of a sensor array in the computer-assisted hand tool in response to at least one feature detected in a time interval during movement of the hand tool in contact with the tissue under examination;
generating a power spectrum of the plurality of signals during the time interval;
locating one or more peak signals within the power spectrum;
compiling the one or more peak signals that comprise a peak value that exceeds a threshold value into a peak signal list;
generating and providing a haptic feedback to a user that is responsive to at least one feature detected in the time interval, wherein the haptic feedback is a dynamic haptic effect comprising parameters that comprise magnitude, frequency and duration;
wherein the parameters of the haptic feedback are based at least in part on a number of peak signals in the peak signal list.

2. The method for performing tissue examination of claim 1 further comprising playing a periodic haptic feedback when the peak signal list comprises at least two peak signals.

3. The method for performing tissue examination of claim 1 further comprising finding the peak signal in the peak signal list having a maximum power, wherein the frequency of the haptic feedback is the frequency of the peak signal having the maximum power.

4. The method for performing tissue examination of claim 1 further comprising computing a Fast Fourier Transform (FFT) of the plurality of signals to generate the power spectrum.

5. The method for performing tissue examination of claim 1 wherein the haptic feedback indicates a deformation of the tissue under examination.

6. The method for performing tissue examination of claim 1 wherein the feature comprises a nodule and the haptic feedback indicates a size of the nodule to the user.

7. The method for performing tissue examination of claim 1 wherein the feature is a blood vessel, and the haptic feedback indicates a location of the blood vessel.

8. The method for performing tissue examination of claim 1 wherein the feature is a luminal structure and the plurality of signals comprise generating an ultrasound signal and detecting an echo signal reflected by the luminal structure.

9. A system for performing minimally invasive tissue examination, comprising:
a computer-assisted hand tool including one or more sensors of a sensor array for receiving a plurality of signals in response to at least one feature detected in a time interval during movement of the hand tool in contact with a tissue under examination;
a memory device for storing a plurality of components containing executable instructions for controlling operation of the computer-assisted hand tool;
a processor cooperative with the executable instructions stored in the memory device for processing each feature and determining a haptic feedback to provide to a user of the computer-assisted hand tool, wherein the haptic feedback is a dynamic haptic effect comprising parameters that comprise magnitude, frequency and duration;
the processor generating a power spectrum of the plurality of signals during the time interval, locating one or more peak signals within the power spectrum, compiling the one or more peak signals that comprise a peak value that exceeds a threshold value into a peak signal list;
an actuator in the computer-assisted hand tool for generating and providing the haptic feedback to the user-wherein the parameters of the haptic feedback are based at least in part on a number of peak signals in the peak signal list.

10. The system for performing tissue examination of claim 9 wherein the actuator plays a periodic haptic feedback when the peak signal list comprises at least two peak signals.

11. The system for performing tissue examination of claim 9 further comprising finding the peak signal in the peak signal list having a maximum power, wherein the frequency of the haptic feedback is the frequency of the peak signal having the maximum power.

12. The system for performing tissue examination of claim 9 wherein the processor performs a Fast Fourier Transform (FFT) of the plurality of signals to generate the power spectrum.

13. The system for performing tissue examination of claim 9 wherein the haptic feedback indicates a deformation of the tissue under examination.

14. The system for performing tissue examination of claim 9 wherein the feature comprises a nodule and the haptic feedback indicates a size of the nodule to the user.

15. The system for performing tissue examination of claim 9 wherein the feature is a blood vessel, and the haptic feedback indicates a location of the blood vessel.

16. The system for performing tissue examination of claim 9 wherein the feature is a luminal structure and the plurality of signals comprise generating an ultrasound signal and detecting an echo signal reflected by the luminal structure.

17. The system for performing tissue examination of claim 9 further comprising a graphical user interface for setting at least one parameter that determines the instructions that are to be executed for controlling operation of the computer-assisted hand tool.

18. A non-transitory computer readable medium for storing instructions, which, when executed by a processor, controls operation of a computer-assisted hand tool during a minimally invasive procedure, the computer readable medium comprising a plurality of instructions for:
receiving and processing a plurality of signals from one or more sensors of a sensor array in the computer-assisted hand tool in response to at least one feature detected in a time interval during movement of the hand tool in contact with the tissue under examination;
generating a power spectrum of the plurality of signals during the time interval;
locating one or more peak signals within the power spectrum;

compiling the one or more peak signals that comprise a peak value that exceeds a threshold value into a peak signal list;

generating and providing a haptic feedback to a user that is responsive to at least one feature detected in the time interval, wherein the haptic feedback is a dynamic haptic effect comprising parameters that comprise magnitude, frequency and duration;

wherein the parameters of the haptic feedback are based at least in part on a number of peak signals in the peak signal list.

19. The non-transitory computer readable medium of claim 18 wherein a periodic haptic feedback is generated when the peak signal list comprises at least two peak signals.

20. The non-transitory computer readable medium of claim 18 further comprising finding the peak signal in the peak signal list having a maximum power, wherein the frequency of the haptic feedback is the frequency of the peak signal having the maximum power.

21. The non-transitory computer readable medium of claim 18 further comprising computing a Fast Fourier Transform (FFT) of the plurality of signals to generate the power spectrum.

\* \* \* \* \*